United States Patent
Rosedale

(10) Patent No.: US 9,610,298 B1
(45) Date of Patent: Apr. 4, 2017

(54) OMEGA-3 FATTY ACID NUTRICEUTICAL COMPOSITION AND OPTIMIZATION METHOD

(71) Applicant: Ronald E Rosedale, Bellevue, WA (US)

(72) Inventor: Ronald E Rosedale, Bellevue, WA (US)

(*) Notice: Subject to any disclaimer, the term of this patent is extended or adjusted under 35 U.S.C. 154(b) by 1 day.

(21) Appl. No.: 14/251,632

(22) Filed: Apr. 13, 2014

Related U.S. Application Data

(63) Continuation of application No. 13/161,495, filed on Jun. 15, 2011, now Pat. No. 8,697,676.

(51) Int. Cl.
| | | |
|---|---|---|
| *A61K 31/683* | (2006.01) | |
| *A61K 31/685* | (2006.01) | |
| *A61K 31/202* | (2006.01) | |
| *A61K 31/215* | (2006.01) | |
| *A61K 31/662* | (2006.01) | |
| *A61K 45/06* | (2006.01) | |
| *G01N 33/50* | (2006.01) | |
| *A23L 1/30* | (2006.01) | |
| *A23L 33/115* | (2016.01) | |
| *A61J 7/00* | (2006.01) | |

(52) U.S. Cl.
CPC .......... *A61K 31/662* (2013.01); *A23L 1/3008* (2013.01); *A61K 31/202* (2013.01); *A61K 31/215* (2013.01); *A61K 31/683* (2013.01); *A61K 31/685* (2013.01); *A61K 45/06* (2013.01); *G01N 33/5088* (2013.01); *A23L 33/115* (2016.08); *A61J 7/00* (2013.01)

(58) Field of Classification Search
None
See application file for complete search history.

(56) References Cited

FOREIGN PATENT DOCUMENTS

| CN | 102724972 A | 10/2012 |
|---|---|---|
| WO | WO2011048493 A1 | 4/2011 |

OTHER PUBLICATIONS

Donald B. Jump, Dietary Unsaturated Fatty Acids and Regulation of Gene Transcription, Curr. Opin. Lipidol. Apr. 2002;13(2):155-64, entire document.
Corton, et. al., "Mimetics of Caloric Restriction Include Agonists of Lipid-activated Nuclear Receptors", J. Biol. Chem. 279 (44), 46204-46212 (2004), entire document.
Harris et. al., "Omega-3 fatty acids and coronary heart disease risk: Clinical and mechanistic perspectives" Atherosclerosis. Mar. 2008; 197(1): 12-24, entire document.

*Primary Examiner* — Savitha Rao
*Assistant Examiner* — Gregg Polansky
(74) *Attorney, Agent, or Firm* — Stephen E. Zweig

(57) ABSTRACT

A novel omega-3 fatty acid/lipid based nutraceutical composition and a method of optimizing said omega-3 fatty acid/lipid based nutraceutical composition. The nutraceutical composition and method is based on the insight that different forms of high omega-3 fatty acid lipids (e.g. triglyceride form, ethyl ester form, free fatty acid form, phospholipid form) have different molecular modes and levels of action. Specifically the phospholipid form is likely more effective at promoting membrane fluidity and permeability, while the free fatty acid form is likely more effective at regulating cell receptors, such as the PPARa receptors, that are responsible for various metabolic effects including lipid metabolism. The desirability of producing omega-3 compositions that may act synergistically and thus more robustly to improve health and to some extent mimic markers of life extension such as shown by caloric restriction, along with specific optimization methods, markers, and compositions are taught.

9 Claims, 2 Drawing Sheets

OMEGA-3 FATTY ACID NUTRICEUTICAL COMPOSITION AND OPTIMIZATION METHOD

CROSS REFERENCE TO RELATED APPLICATIONS

This application is a continuation of U.S. patent application Ser. No. 13/161,495, "OMEGA-3 FATTY ACID NUTRICEUTICAL COMPOSITION AND OPTIMIZATION METHOD", inventor Ronald E. Rosedale, filed Jun. 15, 2011; the contents of which are incorporated herein by reference.

BACKGROUND OF THE INVENTION

Field of the Invention

This invention is in the field of nutriceuticals and nutritional supplements, as well as methods of optimizing the composition of nutriceuticals and nutritional supplements.

Description of the Related Art

Omega-3 Fatty Acids:

Omega-3 fatty acids, also called n-3 poly unsaturated fatty acids (PUFA), have long been suspected of having beneficial effects in humans, particularly with regards to reducing the risk of coronary heart disease, reducing obesity, improving diabetic parameters including blood glucose levels, and improving other parameters of the metabolic syndrome. These fatty acids have a number of beneficial effects, among which is lowering elevated blood triglyceride levels down to more clinically acceptable values (Harris et. al., "Omega-3 fatty acids and coronary heart disease risk: Clinical and mechanistic perspectives" Atherosclerosis. 2008 March; 197(1): 12-24). Omega-3 fatty acids can also assist in weight/fat loss in overweight individuals.

Humans, and indeed essentially all animals, do not synthesize omega-3 fatty acids directly. Instead these fatty acids must be obtained from the diet and therefore are essential dietary nutrients. These fatty acids present in relatively high levels in cold water fish, and other cold water marine animals such as Antarctic krill. The fish themselves do not synthesize the omega-3 fatty acids either, but rather acquire them, usually ultimately from phytoplankton, by virtue of the fish's position on the marine food chain. The commercial omega-3 fatty acids are purified from these marine sources, often by a molecular distillation process to remove unwanted impurities such as mercury, and are sold in both over-the-counter and prescription forms as "fish oil".

The structures of the various omega-3 fatty acids have been reviewed by Rustan and Devon, "Fatty Acids: Structures and Properties" Encyclopedia of Life Sciences (2001). As they discuss, the most common animal fatty acids can be considered to be carbon chains (typically with a length between about 12 to 22 carbons, and often between 18 and 22 carbons long) with one end terminating at a methyl group, and the other end terminating at a carboxyl group.

The saturated fatty acids are all composed of single carbon-carbon bonds, with the rest of the bonds being primarily occupied with hydrogen, while the unsaturated fatty acids have carbon-carbon double bonds at various positions. The positions of the various carbon atoms in the fatty acid chains are numbered with respect to the terminal methyl group, and from a health standpoint, some of the more important unsaturated fatty acids have double bonds starting between the carbon 3 and carbon 4, and are these called n-3 or omega-3 fatty acids. Other important fatty acids have double bonds starting between the carbon 6 and carbon 7 on the chain, and these are called n-6 or omega-6 fatty acids.

Omega-3 fatty acids with a chain length of 20 atoms are called eicosapentaenoic acid (EPA), while omega-3 fatty acids with a chain length of 22 atoms are called docosahexaenoic acid (DHA). EPA is the precursor for a number of different hormone-like molecules, such as the prostaglandins, and it also has an impact on platelet aggregation. EPA and DHA, when incorporated into cell membranes, are also known to increase membrane fluidity, which may make it easier for blood to circulate, and which may be at least partially responsible for their positive effect on cardiovascular health.

Because it is also cumbersome to repeatedly refer to the EPA and DHA form of the omega-3 fatty acids, in general when the term omega-3 fatty acids are used, the term should also be construed as covering at least the most common EPA and DHA forms of these fatty acids.

In addition to marine sources, certain land plants, such as flax (flax seeds), walnuts, and the like also synthesize omega-3 fatty acids as well, but they often synthesize these omega-3 fatty acids in the form of shorter carbon chains (e.g. 18 carbons), such as alpha-linolenic acid (ALA). Although humans and animals can convert the ALA form to the more useful EPA and DHA form, the process is not particularly fast or efficient, and ALA is generally regarded as being a less favorable omega-3 fatty acid, while EPA and DHA, which do not require chain length conversion, are regarded as being more favorable.

The vast majority of the omega-3 fatty acids naturally occurring in fish oil are primarily present in a triglyceride form in which three fatty acid molecules, one or more of which can be an omega-3 fatty acid, and some of which may be non-omega-3 fatty acids, are bound to a three carbon glycerol backbone. This triglyceride form of the omega-3 fatty acids is the same form that is naturally used by the body to transport the omega-3 fatty acids in the blood circulation.

Note that the word "triglycerides" is commonly used in the field to both describe a particular form of omega-3 fatty acid composition, and also to describe blood fats in general, of which a positive effect of the omega-3 fatty acids is to lower the level of (non-omega-3) triglycerides that are circulating in the blood. To avoid confusion, "blood triglycerides" will be used to refer to the medical effect of the omega-3 fatty acids.

Although omega-3 fatty acids are predominantly found in unprocessed fish in a triglyceride form, natural, unprocessed fish oil is not generally used directly as a nutritional supplement due to safety concerns regarding unwanted environmental contaminants such as mercury. To avoid these unwanted contaminants, fish oil processors generally employ molecular distillation techniques to purify and/or concentrate the fish oil.

As a side effect of this molecular distillation process, most of the triglyceride form of the omega-3 fatty acids are converted to a synthetic (not-found in nature) ethyl ester form for encapsulation or bottling. That is, in the purification and concentration process, the various omega-3 fatty acid residue(s) are severed from the glycerol backbone of the triglyceride, and as a result of the process generally used, an artificial ethyl ester form of the omega-3 fatty acid is generated.

In the ethyl ester form, the terminal —OH group of the omega-3 fatty acid head carboxyl group is replaced by an ethyl alcohol —OH—CH2-CH3 group. This modification is considered harmless because once ingested; the user's liver can then, at least eventually, subsequently remove the synthetic alcohol group from the omega-3 fatty acid ethyl ester. However this conversion is neither 100% efficient nor instantaneous.

Alternatively, the manufacturer can, at a higher expense, take the ethyl-ester form of the omega-3 fatty acids, as well as glycerol and other fatty acids, and recreate an artificial omega-3 fatty acid in a triglyceride form that, to all intents and purposes is equivalent to the original natural omega-3 fatty acid in triglyceride form. Nordic Naturals, of Watson California, for example, produces their "Ultimate Omega" line of fish oil products using this approach. Due to the higher expense of this extra process, however, this approach is less common.

Because the ethyl ester form of the omega-3 fatty acids is cheaper to produce, and because manufacturers are understandably reluctant to publicize that they are providing an unnatural form of omega-3 in their nutritional supplements, unless fish oil label clearly says otherwise, it should be assumed that the fish oil contains a high proportion of the omega-3 fatty acids in the ethyl ester form.

Natural fish oil supplements thus generally consist of either the triglyceride form of EPA and DHA form of omega-3 fatty acids, or the synthetic ethyl ester form of EPA and DHA omega-3 fatty acids.

In addition to the natural triglyceride form of omega-3 fatty acids, the natural free fatty acid form of omega-3 fatty acids, and the artificial ethyl ester form of omega-3 fatty acids, another form of omega-3 fatty acids also exists, the phospholipid form.

The phospholipid form of omega-3 fatty acids is found in high concentrations in certain marine animal species adapted for life in extremely cold water, such as Antarctic krill (e.g. *Euphausia superba*). In this form, at least one omega-3 fatty acid residue, often in conjunction with a non-omega-3 fatty acid residue, is again attached to a glycerol backbone, but the third position on the glycerol backbone is occupied by a phosphate group, which in turn is usually conjugated with a choline, serine, or ethanolamine group. Such phospholipid forms of the omega-3 fatty acids likely help the krill continue to function at extremely low temperatures because they help keep the krill cell membranes fluid. In this respect, the phospholipid forms of the omega-3 fatty acids can somewhat considered to be acting like a natural version of a cell membrane antifreeze.

Thus in contrast to standard fish oil, the omega-3 fatty acids in purified Antarctic krill oil supplements generally consists of a mix of around 40%-50% phospholipids (which has omega-3 EPA and DHA carbon chains), and the rest of the omega-3 fatty acid groups are generally found either in the triglyceride form (natural form before molecular distillation) or in the ethyl ester form (after molecular distillation).

Although fish oil has long been a favorite of the nutritional supplement industry in various over-the-counter (non-prescription) forms, recently, the therapeutic utility of the omega-3 fatty acids has also attracted the attention of various pharmaceutical companies. For example, Lovaza, produced by GalaxoSmithKline, is a purified ethyl ester form of the omega-3 fatty acids EPA and DHA. Similarly Epanova, produced by Omthera Pharmaceuticals, is a purified free fatty acid form of the omega-3 fatty acids.

PPAR Receptors:

The omega-3 fatty acids are believed to mediate some of their actions, at least in part, by way of the peroxisome proliferator-activated receptors (PPARs). PPARs are nuclear receptor proteins that bind to retinoid hormones (e.g. hormones built around a carbon chain backbone that is somewhat similar to the carbon chain backbone of omega-3 fatty acids, such as prostaglandins, vitamin D, and relevant to this discussion, also omega-3 fatty acids in the non-esterified, free fatty acid form).

The PPAR receptor proteins are a family of proteins that exist in various forms, called the a, b, d, g1, g2, g3 form. After a PPAR receptor binds its particular ligand, it then forms a dimer with a retinoid Z receptor, and this complex in turn binds to the DNA of various genes, thereby regulating the transcription of these genes.

The PPAR a (alpha) receptors, for example, are primarily expressed in the liver and fat cells (adipose tissues), and play a critical role in both fat metabolism and diabetes. The PPAR g (gamma) receptors are also expressed in adipose tissues as well. Various drugs involved in regulating both triglyceride production and diabetes target various members of the PPAR family. For example, fibrate blood triglyceride lowering drugs target PPARa receptors. By contrast, various anti-diabetic drugs, such as the various thiazolidinediones (exemplified by drugs such as Avandia and Actos) target the PPARg receptors.

Mutations in PPAR receptors have been linked to lipid disorders, insulin resistance, and obesity.

As previously discussed, prior studies have suggested that the omega-3 or n-3 fatty acids may themselves interact with some PPAR receptors. For example, Jump, in "Dietary polyunsaturated fatty acids and regulation of gene transcription", Curr. Opin. Lipidol. 2002 April; 13(2):155-64, reviewed various studies showing that non-esterfied (e.g. free, unbound to glycerol) fatty acids or fatty acid metabolites, in particular 18 and 20 carbon long fatty acids which are n-3 polyunsaturated fatty acids, may activate PPAR receptors, in particular PPARa.

PPARa (PPAR-alpha) is a transcription factor and a major regulator of lipid metabolism in the liver and other organs. Activation of PPARa promotes uptake, utilization, and catabolism of fatty acids by up-regulation and expression of genes involved in fatty acid transport and peroxisomal and mitochondrial fatty acid β-oxidation. PPARa is primarily activated through ligand binding such as by the free fatty acid form of omega-3 fatty acids.

It should be noted that when PPARa is stimulated, it changes the cell's genetic expression and metabolism to an alternate state which better enables fats to be burned as fuel. On the other hand, PPARg (PPAR-gamma) stimulation, as by current diabetic pharmaceuticals, results in the inhibition of fat burning, increased fat storage, and the manufacture of new fat cells. This effect of PPARg is obviously less than desirable for the majority of diabetics and the many overweight people throughout the world. Effective stimulation of PPARa for instance could, on the other hand, present powerful and beneficial benefits.

Caloric Restriction:

Another technique of regulating many metabolic activities in a favorable direction is caloric restriction. Caloric restriction has widely been recognized for over 70 years as being an effective means of prolonging maximal lifespan in many species, including mammals such as rodents, and even primates. As a result, some human enthusiasts have embraced this as a form of life extension protocol. However this life extension protocol, although possibly effective, is very hard to follow.

Caloric restriction diets, which are not generally considered appropriate for individuals under the age of 21, generally require human practitioners to eat between 10-25% fewer calories than average. These diets have been shown to produce impressive health results thus far in humans, including a reduction in cardiovascular disease markers as indicated by LDL particle number and size, coronary artery imaging techniques, carotid artery elasticity. Such diets also increase HDL, lower blood pressure, lower triglyceride levels, and are also associated with improved memory, and reduced inflammation. Because such diets are hard to follow on a long-term basis, however, there is great interest in finding methods to biochemically reproduce the desirable effects of caloric restriction without the hardships of caloric restriction.

Interestingly, recent work suggests that there may be a relationship between caloric restriction and the PPAR receptors. For example, Corton, et. al., "Mimetics of Caloric Restriction Include Agonists of Lipid-activated Nuclear Receptors", J. Biol. Chem. 279 (44), 46204-46212 (2004) studied the impact of caloric restriction on normal and mutant PPARa-null mice. They found that the beneficial effects of caloric restriction were lacking in the PPARa-null mice, suggesting that the PPARa receptors may play a role in mediating the beneficial effects of caloric restriction.

Membrane Fluidity

On a side note, note, but relevant to this invention, a brief review of biological membranes is also in order.

Biological membranes are composed of a bilayer of membrane lipids, primarily cholesterol, glycolipids, and phospholipids. The lipid bilayer structure is thermodynamically favored because hydrophobic effects cause the lipid hydrocarbon chains to coalesce together to form an internal hydrophobic environment inside the membrane, while at the same time, the hydrophilic phosphate polar head groups of phospholipids face the exterior aqueous environment, thus creating a two dimensional lipid bilayer membrane structure.

Because the various lipid molecules are only weakly held into position in the membrane by hydrogen bonds, they are to some extent, free to move around within the two dimensional plane of the membrane. Thus biological membranes act in some respect like a two dimensional fluid. This fluidity is in fact an essential part of the proper biological operation of cells and cell membranes, because it allows embedded cell membrane proteins to move about in a two dimensional space and perform various functions that would otherwise not be possible if they were forced to be stationary.

The fluidity of a biological membrane varies, to some extent, depending on both ambient temperature and lipid composition. At cooler temperatures, such as those experienced by cold blooded marine animals, phytoplankton, and also plants, membrane fluidity is generally much less and more difficult to maintain than it would be in a warm blooded mammal environment.

Thermodynamically, what happens is that at lower temperatures, the hydrogen bonding between the different lipid molecules starts to dominate over the thermodynamic fluctuations that would otherwise cause these bonds to break. To cope with this problem, cold environment plants and marine animals incorporate a larger number of unsaturated omega-3 fatty acid residues in their membrane lipids. The double bonds in the omega-3 fatty acids tend to disrupt or not participate in the hydrogen bonding between different lipids, and thus promote membrane fluidity and again somewhat act like "anti-freeze" in this regard.

Absent specific transport mechanisms, such as transport proteins, pores, and the like, the cell membrane is generally fairly impermeable to most molecules, including free fatty acids, hormones, and the like. However workers, such as Lande et. al. Journal of General Physiology 106, 67-84 (1995) al., have noted that at least for some classes of molecules, higher membrane fluidity is positively correlated with increased permeability. Generally increased fluidity is also likely to help specific transport proteins and membrane receptors function with higher efficiency such as the glucose transporter complex GLUT4 and the insulin receptor, improving control of blood glucose and diabetes.

BRIEF SUMMARY OF THE INVENTION

The invention is based, in part, on the insight that information from the above teaching can be combined to create a model of omega-3 function that predicts that under proper conditions; the various forms (e.g. free fatty acid forms, phospholipid forms) of the omega-3 fatty acids can be combined in a way that produces synergistically favorable health effects. This new omega-3 function model is based on the premise that certain forms (e.g. phospholipid forms) of omega-3 fatty acids are better at enhancing membrane fluidity and permeability, while other forms of omega-3 fatty acids (e.g. free fatty acid forms) are better at stimulating biological receptors of interest, such as the PPARa receptors.

This new omega-3 function model in turn suggests both a new experimental approach for how to better optimize omega-3 fatty acid nutraceuticals, and also suggests new types of omega-3 nutraceutical compositions. The invention is further based on the insight that regardless of whether or not the new omega-3 function model is correct all details, the novel optimization methods and the novel omega-3 nutraceutical compositions have independent value and validity.

The invention is further based, in part, on the insight that it would be desirable to optimize the formulation of omega-3 oils, such as fish oil, to attempt, to the greatest extent possible, to duplicate at least some of the beneficial effects of caloric restriction as a model for improved health.

The invention is also based, in part, on the insight that the new omega-3 function model predicts that prior art omega-3 fatty acid formulations, such as prior art fish oil and/or krill oil formulations and the various pharmaceutical formulations, are not fully optimized. That is, none of the prior art formulations have been optimized for the purpose of delivering the highest effective concentration of omega-3 agonists to suitable health promoting and/or caloric restriction targets, such as the PPARa receptors.

The invention is also based, in part, on the insight that at least some health promoting/caloric restriction receptors, such as the PPARa receptors, are nuclear receptors. Thus to deliver a proper agonist signal to these nuclear receptors not only must the omega-3 be in a form that the receptor recognizes, i.e. the free fatty acid form, but the omega-3 must additionally be in a form that improves membrane fluidity so as to help allow the free fatty acid form of omega-3 to penetrate at least past the cell membrane and often the nuclear membrane as well, and that form of omega-3 would best be as a phospholipid.

The invention is also based, in part, on the insight that an omega-3 formulation optimized, on the one hand, to promote membrane fluidity by delivering an effective amount of omega-3 phospholipid fatty acids, and optimized on the other hand for high levels of PPARa (and other receptor) agonist activity by also delivering an effective amount of the free fatty acid form of omega-3, would have a higher probability to manifest beneficial health effects, such as the health effects associated with caloric restriction.

The invention is also based, in part, on the insight that for maximal effectiveness, the forms of the omega-3 fatty acids that are provided should be directly usable by the body in a manner that requires from the body the fewest number of intermediate enzymatic processing steps. This would be particularly useful because in many chronic disease states, such as obesity, diabetes and cardiovascular diseases, some of these intermediate enzymatic processing steps may not operate with normal efficiency.

DETAILED DESCRIPTION OF THE INVENTION

Figure 1:
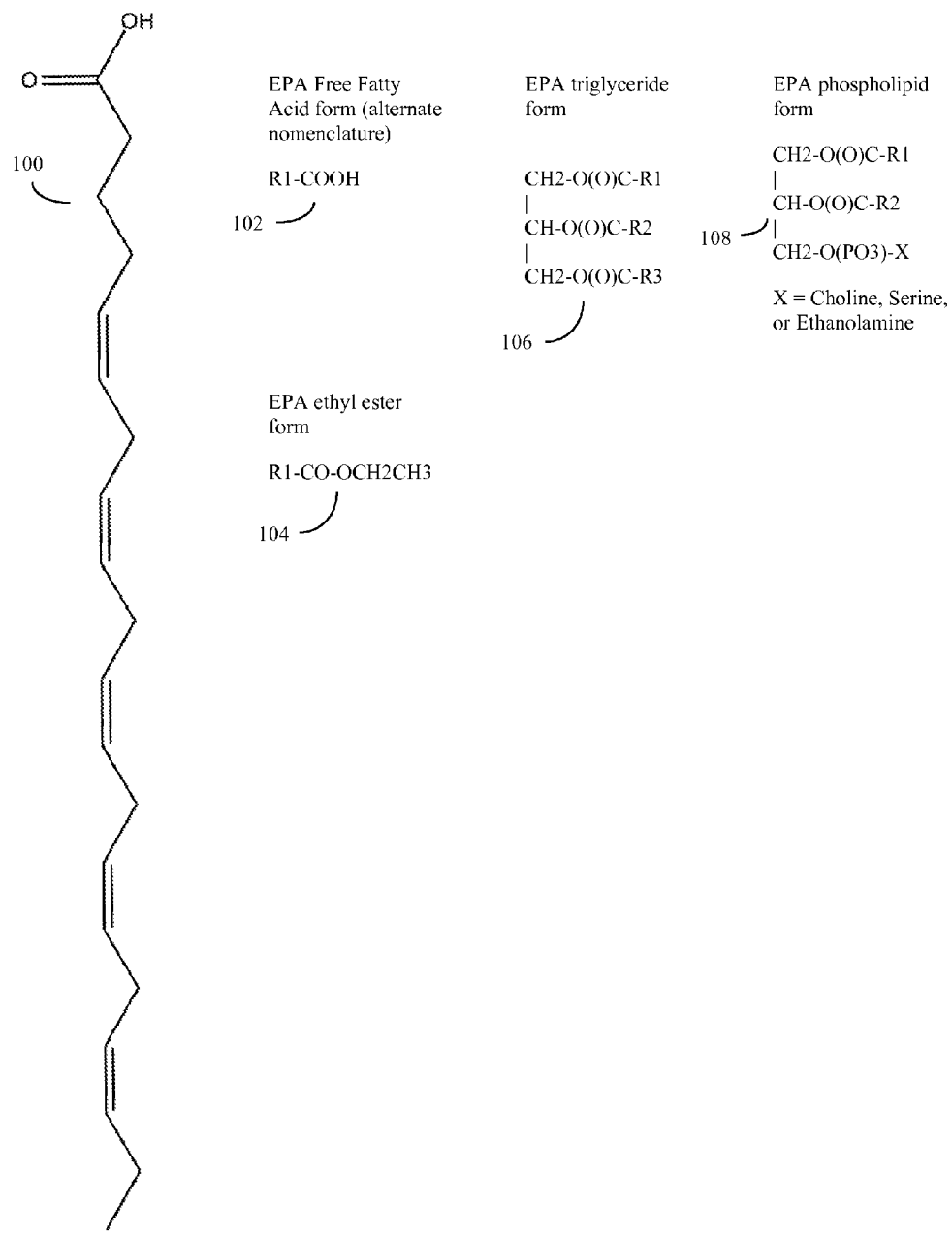
FIG. 1 shows the difference between the free fatty acid forms, ethyl ester forms, triglyceride forms, and phospholipid forms of an omega-3 fatty acid such as EPA.

FIG. 1 shows the difference between the free fatty acid forms, ethyl ester forms, triglyceride forms, and phospholipid forms of an omega-3 fatty acid such as EPA.

Here, the chemical structure of EPA (100) in the free fatty acid form, which is CH3CH2CH=CHCH2CH=CHCH2CH=CHCH2CH=CHCH2CH=CH(CH2)3COOH can be abbreviated as R1-COOH (102). Similarly the chemical structure of EPA in the ethyl ester form can be abbreviated as R1-CO—OCH2CH3 (104).

EPA in the 3-chain glycerol form (106), assuming that only one of the chains R1 is EPA, and the other two chains may be different fatty acids, often common C16 and C18 fatty acids (R2 and R3) is:

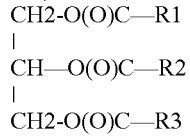

By contrast, EPA in the phospholipid form (108) has the chemical structure:

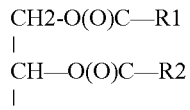

CH2-O(PO3)-X where X may be a side group such as choline, serine, or ethanolamine As previously discussed, manufacturers are usually reluctant to disclose the fact that they have chosen to keep the processed omega-3 fatty acids in their unnatural ethyl ester form. Since there appear to be no government regulations requiring this level of detail to be disclosed, manufacturer labels are often very cryptic in this regard. Although comparative levels of EPA and DHA are reported, the labels otherwise usually fail to specify what form (triglyceride, free fatty acid, or ethyl ester) the omega-3 fatty acids are in.

As a result, the terminology and literature in this field can be highly confusing, and citations must be read carefully. Usually the simple term "fatty acids" generally refers to the basic carbon chain backbone of the molecule(s), rather than the specific form of this basic carbon chain backbone. To reiterate, when the omega-3 fatty acids are in the form of the carboxylic acid and also not attached or "esterified" to a glycerol backbone as part of a triglyceride, they are termed "free fatty acids". When the omega-3 fatty acids have an ethyl ester attached, they are termed omega-3 acid ethyl ester". Similarly the omega-3 fatty acid molecule can also be attached to a 3 carbon glycerol backbone with two other fatty acids (omega-3 or not) and form a three carbon chain triglyceride, or the omega-3 fatty acid molecule can be attached to a glycerol backbone that has another fatty acid attached, along with a phosphate residue on the $3^{rd}$ carbon, and form a phospholipid.

The one partial exception to the ambiguity in disclosure is krill oil, where phospholipid forms of the omega-3 fatty acids are particularly valued. Here manufacturers usually at least report on the percentage of the oil that is in the phospholipid form. Here again, however, manufacturers will still typically fail to disclose the exact form of the remainder of the composition, or even specify how much of the phospholipid has EPA or DHA residues. Thus, although percentages of phospholipids and percentage of EPA and DHA may be reported, the specific forms of the EPA and DHA (percentage in triglyceride, ethyl ester, etc.) will again usually not be reported, or likely even known. Here again, the presumption should be that unless otherwise reported, a high proportion of the ethyl ester form should be assumed.

Indeed the few manufacturers, such as Nordic Naturals, who use natural and more expensive triglyceride forms of EPA and DHA, usually announce these alternative forms by very prominent labeling in order to draw attention to this fact.

Figure 2:
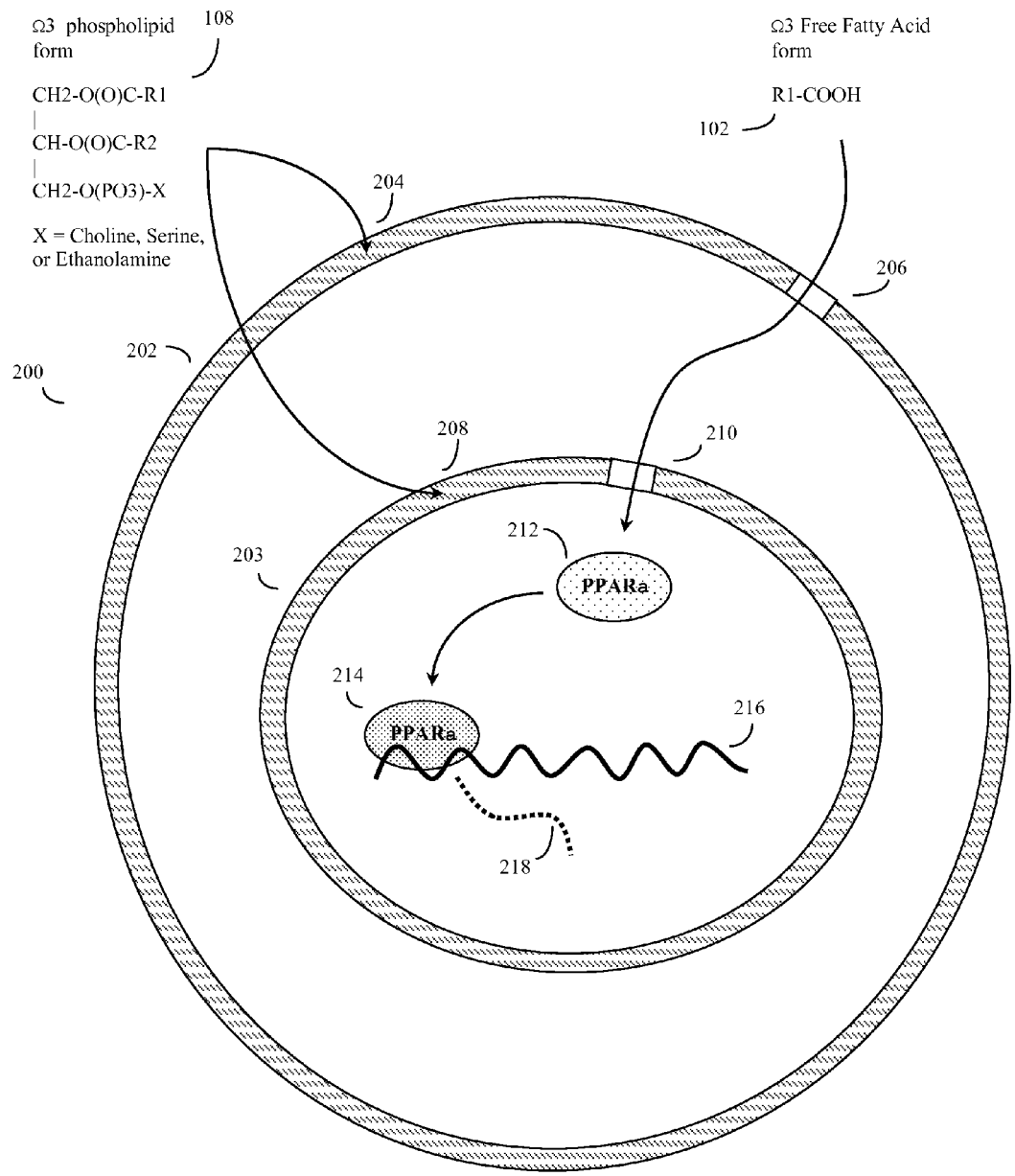
FIG. 2 shows a simplified diagram of the model of omega-3 function which inspired both the invention's nutraceutical compositions and optimization methods. Here the phospholipid forms of omega-3 fatty acids promote membrane fluidity and omega-3 free fatty acid uptake, while the free fatty acid form of omega-3 then serves (for example), as a PPARa receptor agonist. In this model, the phospholipid form of omega-3 fatty acids and the free fatty acid form of omega-3 fatty acids thus act synergistically, as the phospholipid form of omega-3 fatty acids makes it easier for the free fatty acid form of omega-3 fatty acids to reach the membrane-protected PPARa receptors. Here Omega-3 is abbreviated as Ω3.

FIG. 2 shows the proposed molecular mechanism that inspired the invention's novel omega-3 fatty acid composition and optimization method. In this model, the phospholipid forms of omega-3 fatty acids promote membrane fluidity and omega-3 free fatty acid uptake. By contrast, the free fatty acid form of omega-3 then can serve, for example, as agonists (stimulators) for PPARa receptors and/or other nuclear, cytoplasmic, or cell surface membrane receptors.

In this model, consider a cell, such as a liver cell (200). The cell has a cell membrane (202) and a nuclear membrane (203). Here the phospholipid form of the omega 3 fatty acids (108) can be incorporated "as is" (i.e. with little or no enzymatic alteration by the body) into both the cell membrane (204) and the nuclear membrane (208), increasing both membrane fluidity and membrane permeability (206), (210). As a result, aided or synergized by this increased membrane fluidity and permeability, the free fatty acid form of the omega-3 fatty acids (102) can now more effectively permeate or be transported across the cell membranes (202) and (203) "as is". Once inside the cytoplasm or nucleus, the free fatty acid form of the omega-3 fatty acids is now free to act as an agonist or stimulator of receptors, such as PPARa receptors (212). Once stimulated, the PPARa receptors (214) or other receptors can in turn mediate other cellular pathways. In this particular example, the activated PPARa receptor (214) binds to one or more regions of the cellular DNA (216), and stimulates transcription of one or more genes (218).

This model suggests both that the various forms of the omega-3 fatty acids do not act by the same mechanism, and further that some forms, such as the triglyceride form of omega-3 fatty acids and the ethyl ester form of omega-3 fatty acids are possibly less effective at some of these functions. In this model, for example, neither the triglyceride form nor the ethyl ester form, "as is", is envisioned as being as effective at either stimulating membrane fluidity or stimulating receptors such as PPARa receptors. This model thus makes a prediction that the triglyceride form of the omega-3 fatty acids and the ethyl ester form of the omega-3 fatty acids may be less favored for this type of application. Furthermore, though the phospholipid form of omega-3 might be best at enhancing membrane fluidity and permeability, is not likely to be best at stimulating receptors. Likewise, though the free fatty acid form of omega-3 fatty acids are likely the best form, and possibly the only form, that can stimulate receptors such as PPARa, it is not likely to be the form best at enhancing membrane fluidity, as this would require in vivo modification to the phospholipid form.

The limitations of the model should be appreciated, however. The model has value in that it predicts both a new optimization method and a new omega-3 nutraceutical combination. However since both the optimization method and the new omega-3 nutraceutical combinations have value independent of the model itself, other omega-3 forms may also be studied by the proposed optimization method and also explored as various alternative omega-3 nutraceutical combinations. Thus, use of both the triglyceride form and the ethyl ester form of omega-3 fatty acids is not disclaimed, and indeed in some alternative formulations, positive synergistic effects may potentially be seen with either the triglyceride form or the ethyl ester form as well.

Thus the model constitutes a valid scientific hypothesis which in turn suggests both novel optimization methods and new compositions. Thus the specific PPAR receptor teaching and membrane fluidity teaching discussed here should be considered to be only one example of an aspect or embodiment of the invention, and is not intended to be limiting.

A table showing how the invention's omega-3 fatty acid nutraceutical formulation contrasts with prior art prescription and over-the-counter omega-3 fatty acid nutraceutical formulations is shown in Table 1:

TABLE 1

Various forms of omega-3 fatty acids in prior-art omega-3 fatty acid formulations, versus the invention's omega-3 fatty acid formulation.

| | omega-3 fatty acid forms: | | | |
|---|---|---|---|---|
| | omega-3 free fatty acids | omega-3 ethyl ester | omega-3 triglycerides | omega-3 phospholipids |
| Fish oil (natural) | — | — | Nearly 100% | — |
| Fish oil (molecular distillation) | — | Nearly 100% | — | — |
| Krill oil (natural) | — | — | Roughly 50% | Roughly 50% |
| Krill oil (molecular distillation) | — | Roughly 50% | — | Roughly 50% |
| Epanova | Nearly 100% | — | — | — |
| Lovaza (pharmaceutical grade molecular distillation) | — | Nearly 100% | — | — |
| Nordic Naturals (reconstituted triglycerides) | — | — | Nearly 100% | — |
| Invention | 20-70% | — | — | 20-70% |

In one embodiment, the invention may be a nutraceutical dietary supplement or food comprising the phospholipid form of omega-3 fatty acids (including EPA and DHA) and the free fatty acid form of omega-3 fatty acids. In general, the phospholipid form of omega-3 fatty acids will comprise between about 20 and 70 percent of the omega-3 fatty acids in the nutraceutical supplement, the free fatty acid form of omega-3 fatty acids will comprise between 20 and 70 percent of the omega-3 fatty acids in the nutraceutical supplement, the triglyceride form of omega-3 fatty acids will comprise between 0 and 5% of the omega-3 fatty acids in the nutraceutical supplement, and the ethyl ester form of the omega-3 fatty acids will comprise between 0 and 5% of the omega-3 fatty acids in the nutraceutical supplement.

In this supplement, the sum of all omega-3 fatty acids forms may also be equal to between 10 to 100% of the entire composition, and the remainder of the dietary supplement will be comprised of other materials such as other triglycerides or fatty acids such as medium chain triglycerides or monounsaturated fats, antioxidants, emulsifiers (e.g. lecithin), carriers (e.g. gelatin, water), and the like.

Here, the specific amounts of the phospholipid form of the omega-3 fatty acids and the specific amounts of the free fatty acid forms of the omega-3 fatty acids may be adjusted so that the enhanced membrane fluidity and permeability afforded by the omega 3 phospholipid form of the fatty acids results in greater proportions of the free fatty acid form of omega-3 fatty acids penetrating cellular membranes. After penetration, the free fatty acid form of the omega-3 fatty acids may then bind to the nuclear PPARa receptors for example, or other receptors or molecular effectors such as genetic transcription factors, thus creating an agonistic effect on these receptors and/or effectors. In other words, the membrane fluidity and permeability enhancement properties of the phospholipid form of the omega-3 fatty acids will synergize with the PPARa or other receptor or other biochemical effects of the free fatty acid form of the omega-3 fatty acids, thus creating increased PPARa (and/or other) receptor activation (or other biochemical effects) than would be possible if either the phospholipid form or the free fatty acid form of the omega-3 fatty acids were used separately.

Unsaturated fatty acids, such as the omega-3 fatty acids, oxidize rapidly in air, and often the nutraceutical supplement may also contain various materials intended to retard oxidation, such as vitamin E, tocopherols, tocotrienols, lipoic acid, astaxanthin, and other fat soluble antioxidants, as well as CoQ10, l-carnitine, acetyl l-carnitine, medium and short chain triglycerides. Additionally, the other materials may also comprise materials such as medium and short chain fatty acids, omega-6 fatty acids, omega-9 fatty acids, choline, cholesterol, gelatin, and water.

In general, the nutraceutical supplement may be formulated so that the percentage of the phospholipid form of omega-3 fatty acids and the percentage of the free fatty acid form of the omega-3 fatty acids are chosen based on their positive synergistic effect when taken by an adult human at a level of between about 1 gm and 30 gm (or two tablespoons) of the supplement on a daily basis. In some embodiments, at least some of the phospholipid form of the omega-3 fatty acids may be derived from Antarctic Krill oil. In other embodiments, least some of the phospholipid form of the omega-3 fatty acids may be derived from algae, phytoplankton, or other vegetarian source. In some embodiments, at least some of the triglyceride form of the omega-3 fatty acids may be derived from fish oil. In some embodiments, at least some of the triglyceride form of the omega-3 fatty acids may be derived from algae, phytoplankton, or other vegetarian source.

The optimal levels of omega-3 phospholipid forms of the fatty acids and omega-3 free fatty acid forms may be determined by various means, including animal studies. Here, for example, the methods of Corton et. al. (Journal of Biological Chemistry 279 (44), 46204-46212 (2004) may be used. Test animals such as mice, or even human subjects, may be fed a controlled diet containing various formulations of the nutritional supplement where the omega-3 fatty acids are set at various phospholipid to free fatty acid concentrations. The levels of gene expression (transcription) by the various lipid activated nuclear receptors, such as the PPARa receptors, may then be monitored using standard methods such as reverse transcriptase-PCR methods as detailed by Corton. These gene transcription levels, which may be considered to be one type of surrogate endpoint associated with life extension, can then be analyzed versus the omega-3 phospholipid to omega-3 free fatty acid composition of various nutritional supplement candidates, and the formulation associated with the highest level of gene expression, such as the highest level of PPARa activation, may be chosen.

In addition to looking directly at the transcription levels of certain genes associated with life extension, other markers of life extension may also be monitored, and the levels of omega-3 phospholipid to omega-3 free fatty acid associated with the desired effect (often the greatest effect at which unwanted side effects that do not also occur) may be chosen. These can be surrogate endpoints associated with life extension protocols such as caloric restriction, and can include endpoints or markers associated with reduced free T3 levels, reduced fasting serum insulin levels, reduced fasting serum leptin levels, reduced basal body temperature, reduced serum triglycerides, and enhanced beta fatty acid oxidation as indicated via a reduced respiratory quotient.

Although in principle, any positive synergistic effect produced by a combination of the phospholipid form and the free fatty acid form of the omega-3 fatty acids would be detected by the above methods, and would be also quite acceptable in terms of the actual formulation. In particular, one synergistic effect that is expected according to the invention is where the synergistic effect is due to the free fatty acid form of omega-3 fatty acids penetrating the cellular membranes at a higher rate due to increased cell membrane permeability and/or fluidity induced by the combined phospholipid form of the omega-3 fatty acids.

Also in principle, any positive synergistic effect on any agonistic effect induced on any biochemical receptor (and/or other molecular effector such as an enzyme or genetic transcription factor directly) would also be quite acceptable in terms of the actual formulation. However as previously discussed, in particular one synergistic effect may be due to the phospholipid form of omega-3 lipid's promotion of the ability of the free fatty acid form of omega-3 fatty acids to function as a biochemical agonist for receptors and/or genetic transcription factors, in particular as an agonist to PPAR nuclear receptors such as the PPARa nuclear receptors.

Alternatively, the invention may be viewed as a method for optimizing the composition of the omega-3 free fatty acids of a nutraceutical.

Although typically, the nutraceutical supplement will be delivered in a pill form, often in the form of one or more pills that may deliver between 300 mg and 1000 mg of total oil per pill, of which often between 25% to 100% of this oil may be the various forms of omega-3 fatty acids discussed previously. In some embodiments, instructions for use instructing that the nutraceutical should be taken by an adult human at a level of between 0.5 gm and 30 gm of said nutraceutical on a daily basis may also be provided. However other forms of nutritional supplement may also be used. It may also be delivered as a bottled oil food or supplement to be taken by spoonful. In alternative formulations, the nutritional supplement may be blended into other food products (e.g. peanut butter, margarine, salad oil, various drinks, and the like). In other formulations, the nutritional supplement may be incorporated into various solid foods, or even delivered in a formulation suitable for enteric tube feeding or intravenous administration.

Trademarks: LOVAZA is a registered trademark of GLAXOSMITHKLINE LLC LIMITED LIABILITY COMPANY DELAWARE; EPANOVA is a registered trademark of Chrysalis Pharma AG CORPORATION SWITZERLAND; and covers ULTIMATE OMEGA is a registered trademark of Nordic Naturals, Inc. CORPORATION CALIFORNIA.

The invention claimed is:

1. A nutraceutical comprising the phospholipid form of omega-3 fatty acids and the triglyceride form of omega-3 fatty acids;
   wherein said nutraceutical is an artificial mixture of purified omega-3 fatty acids from different sources;
   wherein the phospholipid form of omega-3 fatty acids, at least some derived from a first source, comprise between 20 and 70 percent of the total omega-3 fatty acids, the triglyceride form of omega-3 fatty acids, at least some derived from a different source, comprise between 20 and 70 percent of the total omega-3 fatty acids, the free fatty acid form of omega-3 fatty acids comprise between 0 and 5% of the total omega-3 fatty acids, the ethyl ester form of omega-3 fatty acids comprise between 0 and 5% of the total omega-3 fatty acids; and wherein the sum of all omega-3 fatty acids is equal to 100%, and the remainder of the nutraceutical is comprised of other materials; and
   wherein said omega-3 fatty acids comprise EPA and DHA.

2. The nutraceutical of claim 1, wherein said other materials comprise one or more materials selected from the group consisting of vitamin E, tocopherols, tocotrienols lipoid acid, astaxanthin, other fat soluble antioxidants, CoQ10, l-carnitine, acetyl l-carnitine, medium and short chain triglycerides, omega-9 fatty acids, choline, cholesterol, gelatin, and water.

3. The nutraceutical of claim 1, wherein said nutraceutical is provided in a pill form along with instructions for use instructing that the nutraceutical should be taken by an adult human at a level of between 0.5 gm and 30 gm of said nutraceutical on a daily basis.

4. The nutraceutical of claim 1, wherein at least some of said phospholipid form of omega-3 fatty acids are derived from Antarctic Krill oil.

5. The nutraceutical of claim 1, wherein at least some of said phospholipid form of omega-3 fatty acids are derived from algae, phytoplankton, or other vegetarian source.

6. The nutraceutical of claim 1, wherein at least some of said triglyceride form of omega-3 fatty acids are derived from fish oil.

7. The nutraceutical of claim 1, wherein at least some of said triglyceride form of omega-3 fatty acids are derived from algae, phytoplankton, or other vegetarian source.

8. The nutraceutical of claim 1, configured in the form of a pill comprising between 75 mg and 1000 mg of total omega-3 fatty acids per pill.

9. The nutraceutical of claim 1, further using a molecular distillation process to remove mercury from at least one of said first or different sources.

\* \* \* \* \*